(12) United States Patent
Seth et al.

(10) Patent No.: US 7,622,180 B2
(45) Date of Patent: *Nov. 24, 2009

(54) NET HOOK FASTENERS (75) Inventors: Jayshree Seth, Woodbury, MN (US); Janet A. Venne, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/456,234

(22) Filed: Jul. 10, 2006

(65) Prior Publication Data

US 2008/0009821 A1    Jan. 10, 2008

(51) Int. Cl.
*B32B 3/06* (2006.01)

(52) U.S. Cl. .............. 428/100; 24/442; 442/2; 442/49

(58) Field of Classification Search ............... 428/100; 24/442; 442/2, 49
See application file for complete search history.

(56) References Cited

U.S. PATENT DOCUMENTS

| | | | |
|---|---|---|---|
| 2,919,467 A | 1/1960 | Mercer | |
| 3,085,292 A | 4/1963 | Kindseth | |
| 3,266,113 A | 8/1966 | Flanagan, Jr. | |
| 3,365,352 A | 1/1968 | Van Burleigh et al. | |
| 3,387,069 A | 6/1968 | Stohr | |
| 3,394,431 A | 7/1968 | Nalle, Jr. | |
| 3,397,428 A | 8/1968 | Donald | |
| 3,398,431 A | 8/1968 | Corbett | |
| 3,447,207 A | 6/1969 | Danze | |
| 3,448,183 A | 6/1969 | Chisholm | |
| 3,485,912 A | 12/1969 | Schrenk et al. | |
| 3,488,415 A | 1/1970 | Patchell et al. | |
| 3,515,778 A | 6/1970 | Fields et al. | |
| 3,525,785 A | 8/1970 | Fairbanks | |
| 3,554,853 A | 1/1971 | Mercer | |
| 3,557,413 A | 1/1971 | Engle | |
| 3,594,870 A | 7/1971 | Schippers et al. | |
| 3,632,269 A | 1/1972 | Doviak et al. | |
| 3,683,059 A | 8/1972 | Fairbanks | |
| 3,756,758 A | 9/1973 | Prall | |
| 3,781,398 A | 12/1973 | Erb | |
| 3,920,365 A | 11/1975 | Mules | |
| 3,932,090 A | 1/1976 | Brumlik | |
| 3,952,127 A | 4/1976 | Orr | |
| 4,001,366 A | 1/1977 | Brumlik | |
| 4,056,593 A | 11/1977 | De Navas Albareda | |
| 4,059,713 A | 11/1977 | Mercer | |
| 4,075,379 A | 2/1978 | Lloyd | |
| 4,083,914 A | 4/1978 | Schippers et al. | |
| 4,101,625 A | 7/1978 | Haley | |
| 4,135,021 A | 1/1979 | Patchell et al. | |

(Continued)

FOREIGN PATENT DOCUMENTS

DE    295 14 350    11/1995

(Continued)

*Primary Examiner*—Alexander Thomas (57) ABSTRACT

The present invention concerns a polymeric film hook netting comprising a continuous film backing having a net section formed of plurality of a first set of thermoplastic strands extending in a first direction and a second set of integral strands extending in a second direction at least one of which strands has upstanding hook elements and a second integral non-net film section.

18 Claims, 4 Drawing Sheets

U.S. PATENT DOCUMENTS

| | | |
|---|---|---|
| 4,189,809 A | 2/1980 | Sotos |
| 4,190,692 A | 2/1980 | Larsen |
| 4,197,069 A | 4/1980 | Cloeren |
| 4,201,814 A | 5/1980 | Gilbert et al. |
| 4,207,375 A | 6/1980 | Kim et al. |
| 4,285,100 A | 8/1981 | Schwarz |
| 4,300,562 A | 11/1981 | Pieniak |
| 4,329,309 A | 5/1982 | Kelly |
| 4,368,565 A | 1/1983 | Schwarz |
| 4,426,344 A | 1/1984 | Dinter et al. |
| 4,440,709 A | 4/1984 | Rasmussen |
| 4,492,549 A | 1/1985 | Rasmussen et al. |
| 4,533,510 A | 8/1985 | Nissel |
| 4,536,362 A | 8/1985 | Donaldson et al. |
| 4,636,419 A | 1/1987 | Madsen et al. |
| 4,732,723 A | 3/1988 | Madsen |
| 4,755,247 A | 7/1988 | Mudge |
| 4,787,897 A | 11/1988 | Torimae et al. |
| 4,832,834 A | 5/1989 | Baird, Jr. |
| 4,842,794 A | 6/1989 | Hovis |
| 4,894,060 A | 1/1990 | Nestegard |
| 5,011,642 A | 4/1991 | Welygan et al. |
| 5,120,484 A | 6/1992 | Cloeren |
| 5,173,141 A | 12/1992 | Leseman et al. |
| 5,179,767 A | 1/1993 | Allan |
| 5,209,282 A | 5/1993 | Franco et al. |
| 5,344,691 A | 9/1994 | Hanschen et al. |
| 5,354,597 A | 10/1994 | Capik et al. |
| 5,429,856 A | 7/1995 | Krueger et al. |
| 5,462,708 A | 10/1995 | Swenson et al. |
| 5,468,428 A | 11/1995 | Hanschen et al. |
| 5,501,675 A | 3/1996 | Erskine |
| 5,555,608 A | 9/1996 | Allan et al. |
| 5,605,729 A | 2/1997 | Mody et al. |
| 5,607,635 A | 3/1997 | Melbye |
| 5,616,394 A | 4/1997 | Gorman et al. |
| 5,667,869 A | 9/1997 | Beretta |
| 5,792,408 A | 8/1998 | Akeno |
| 5,840,412 A | 11/1998 | Wood et al. |
| 5,885,686 A | 3/1999 | Cederblad |
| 5,891,549 A | 4/1999 | Beretta et al. |
| 5,976,665 A | 11/1999 | Hansson |
| 6,132,660 A | 10/2000 | Kampfer |
| 6,209,177 B1 | 4/2001 | Murasaki |
| 6,221,483 B1 | 4/2001 | Hilston et al. |
| 6,245,401 B1 | 6/2001 | Ying et al. |
| 6,368,097 B1 | 4/2002 | Miller et al. |
| 6,511,742 B1 | 1/2003 | Mussig et al. |
| 6,669,887 B2 | 12/2003 | Hilston et al. |
| 7,134,192 B1 | 11/2006 | Savicki |
| 7,241,483 B2 * | 7/2007 | Ausen et al. ............... 428/100 |
| 2002/0112325 A1 | 8/2002 | Keohan et al. |
| 2002/0195738 A1 | 12/2002 | Norquist et al. |
| 2003/0034583 A1 | 2/2003 | Provost |
| 2003/0096548 A1 | 5/2003 | Groitzsch et al. |
| 2003/0203155 A1 | 10/2003 | Kobe et al. |
| 2005/0003151 A1 | 1/2005 | Jacoby |
| 2005/0060849 A1 | 3/2005 | Vanbenschoten et al. |
| 2005/0079315 A1 | 4/2005 | Seth et al. |
| 2005/0079321 A1 | 4/2005 | Tuman et al. |

FOREIGN PATENT DOCUMENTS

| | | |
|---|---|---|
| DE | 201 04 988 | 10/2001 |
| EP | 0 096 458 | 12/1983 |
| EP | 0 160 857 | 4/1985 |
| EP | 0 191 355 | 8/1986 |
| EP | 0 363 064 B1 | 1/1997 |
| EP | 0 836 929 | 4/1998 |
| JP | 6-293067 | 4/1993 |
| JP | 8-187113 | 7/1996 |
| KR | 1998-0000866 | 3/1998 |
| WO | WO 93/09690 | 5/1993 |
| WO | WO 99/10166 | 3/1999 |
| WO | WO 01/47697 A1 | 7/2001 |
| WO | WO 2005/122818 A1 | 12/2005 |
| WO | WO 2005/123363 A1 | 12/2005 |

* cited by examiner

NET HOOK FASTENERS

FIELD OF THE INVENTION

The present invention concerns an extrusion formed reticulated web, mesh or netting, which can be formed as reticulated hook fasteners for use with hook and loop fasteners.

BACKGROUND OF THE INVENTION

Formation of net structures from a profile extruded film is disclosed in US patent Applications 2004/0170802 and 2004/0170801 where a film is provided with integral ribs. The film backing is cut at a angle transverse to the ribs forming a first set of strands for the netting. The second set of strands is formed from the coextruded ribs. Following the cutting step the film is elongated in the transverse direction to the cut, generally along the length of the coextruded ribs opening the film up to create the netting. Hooks can be formed on the net strands formed by this method by providing profiled ridges with hook profiles that are also cut during the net formation process. This is a continuous method and creates a strong net hook structure. Incorporating this net hook into a fastening tab structure however is difficult.

SUMMARY OF THE INVENTION

The present invention is directed at a hook fastening tab net structure formed from polymer netting formed from an extruded film. The extruded film netting has a first hook net section which is three dimensional, and has a first face and a second face and a second substantially planar second non-net section. The extruded film forming the netting is intermittently cut in regular intervals along a cut line dimension on one or more faces or alternatively in alternating fashion on the first face and the second face in the three dimensional section, but not through at least a portion of a planar backing section that becomes the non-net section. At least one face of the three dimensional section has a plurality of profiled ridges or ribs that have the cross-sectional profile of a hook head, and extend at least partially transverse to the cut line dimension. The cut film is then stretched (oriented) at least partially transverse to the cut line dimension creating a hook netting characterized by net strands extending in the cut line dimension which strands have a width preferably substantially equal to the hook head width, and an integral non-net section. By "integral", as defined for this invention, it is meant that the net section and non-net sections or the various strands are contiguous, boundaryless structures formed from the same polymer film backing, i.e. without seams, bonding or the like. Integral would not mean side-by-side connected materials, laminates of two or more materials or the like. The polymer netting is preferably made by a novel adaptation of a known method of making hook fasteners as described, for example, in U.S. Pat. Nos. 3,266,113; 3,557,413; 4,001,366; 4,056,593; 4,189,809 and 4,894,060 or alternatively U.S. Pat. No. 6,209,177, the substance of which are incorporated by reference in their entirety.

The preferred method generally includes extruding a thermoplastic resin through a die plate, which die plate is shaped to form a nonplanar or three dimensional film section which could be either a backing with a regularly oscillating peak and valley base structure that oscillates from a top surface to a bottom surface forming longitudinally extending ridges using both faces of the film, or a substantially planer base with ridges or ribs extending from at least one and generally both faces of the base, and a second substantially planar backing section. This planar section could also have ridges or ribs on one or both faces but will have a substantially planar backing that would not be cut in the subsequent cutting step forming the net section from the three dimensional section. The hook netting section is formed by transversely cutting through the film three dimensional film section in the thickness dimension (Z dimension) at spaced intervals along a length (X dimension), at a transverse angle, to form discrete cut portions. The cuts can be on one or both faces of the three dimensional film and are at least through the ridges having a hook head profile. Subsequently, longitudinal stretching of the film (in the direction of the ridges or the X dimension or direction) separates these cut portions of the three dimensional film backing, which cut portions then form one set of strands or legs of the hook netting, namely the transverse extending strands or legs (Y dimension) of the hook netting. The ridges, or continuous uncut regions of an oscillating backing, between the cut lines on an uncut face create lands or strands, and these uncut portions of the ridges or backing form the lengthwise strands (X dimension) of the hook netting section.

BRIEF DESCRIPTION OF THE DRAWINGS

The present invention will be further described with reference to the accompanying drawings wherein like reference numerals refer to like parts in the several views, and wherein.

DETAILED DESCRIPTION OF ILLUSTRATIVE EMBODIMENTS OF THE INVENTION

Figure 1:
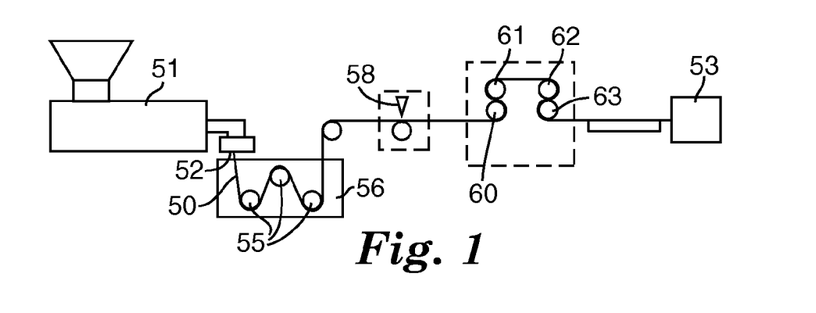
FIG. 1 is a schematic view of a method of forming the invention netting.
Figure 2:
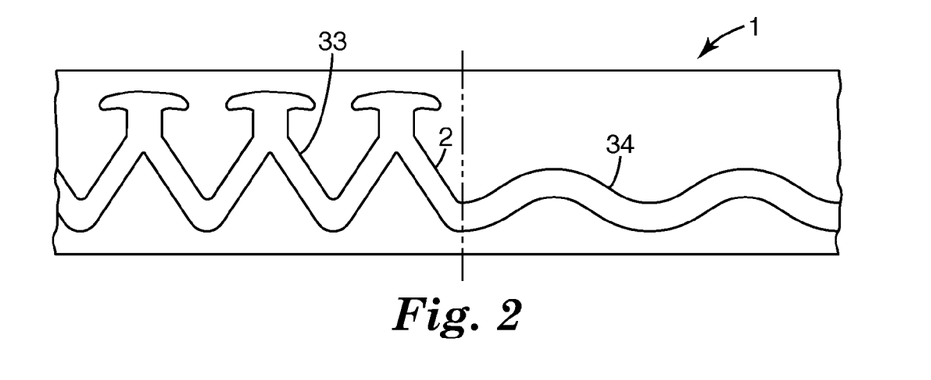
FIG. 2 is a cross-sectional view of a die plate used to form a precursor film used in accordance with the present invention.
Figure 3:
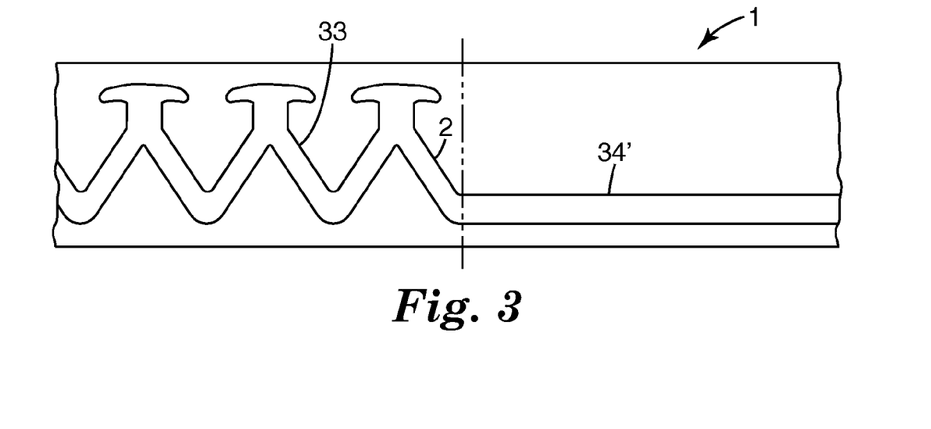
FIG. 3 is a cross-sectional view of a die plate used to form a precursor film used in accordance with the present invention.
Figure 4:
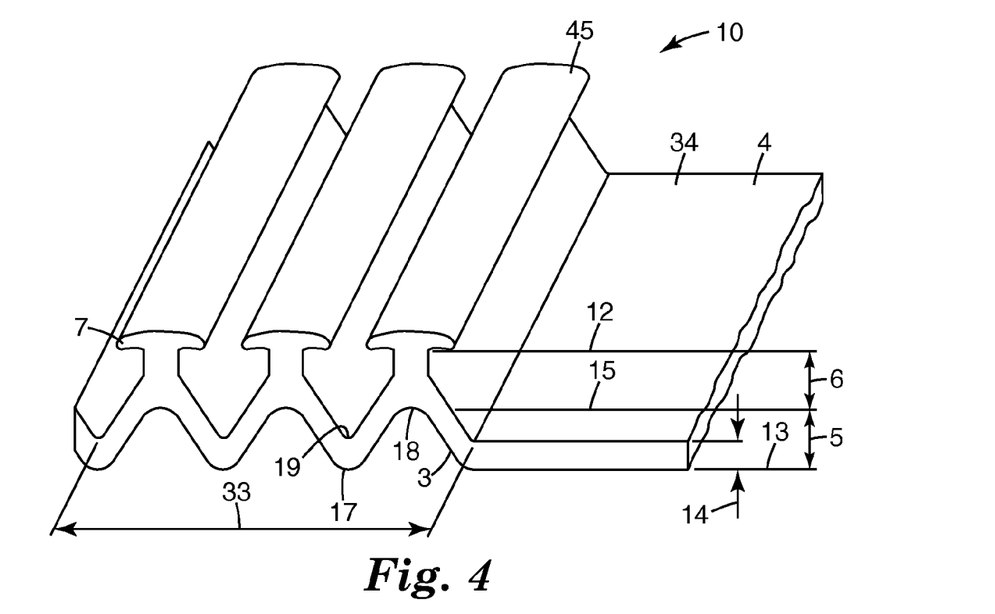
FIG. 4 is a perspective view of a first embodiment precursor film in accordance with the present invention.
Figure 5:
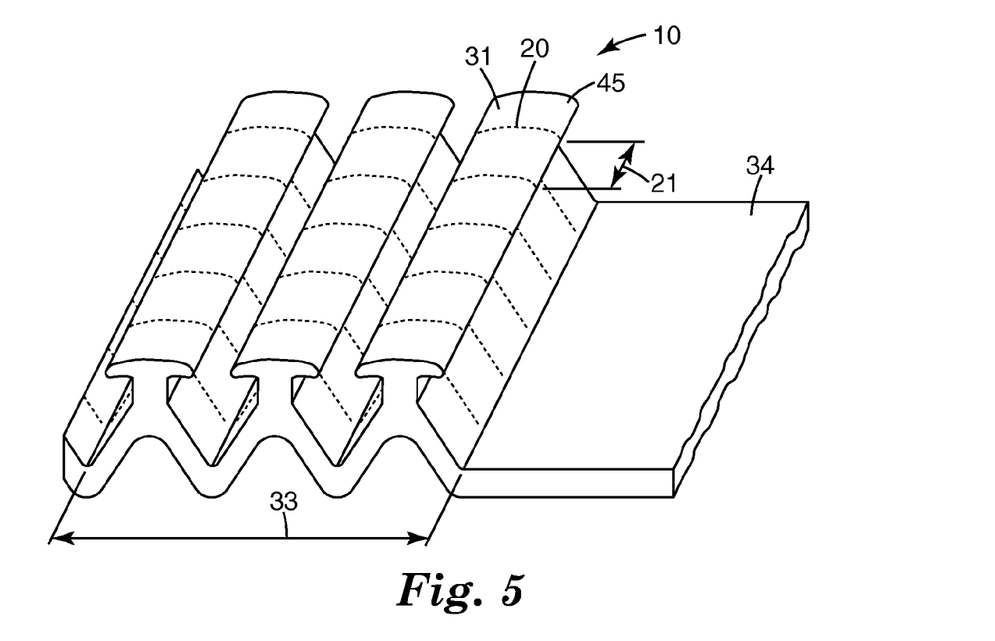
FIG. 5 is a perspective view of the FIG. 4 film cut on one face at regular intervals.
Figure 6:
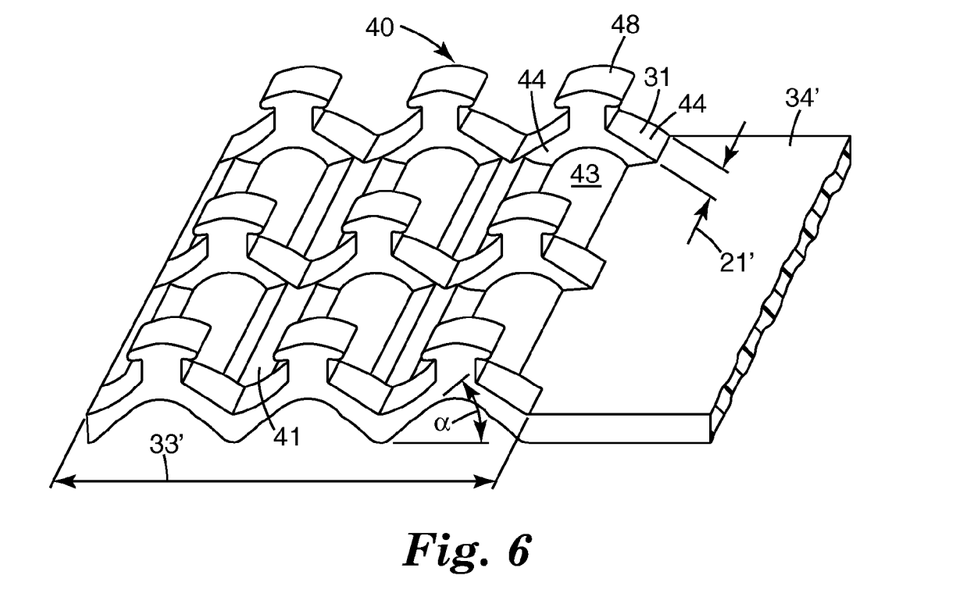
FIG. 6 is a perspective view of a netting in accordance with the present invention having hook elements.
Figure 7:
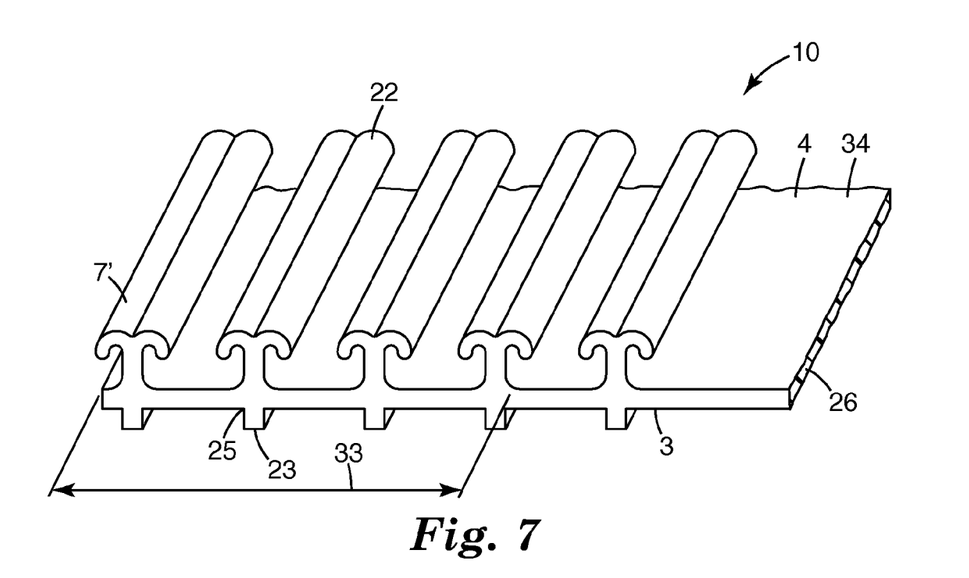
FIG. 7 is a perspective view of another embodiment precursor film in accordance with the present invention.
Figure 8:
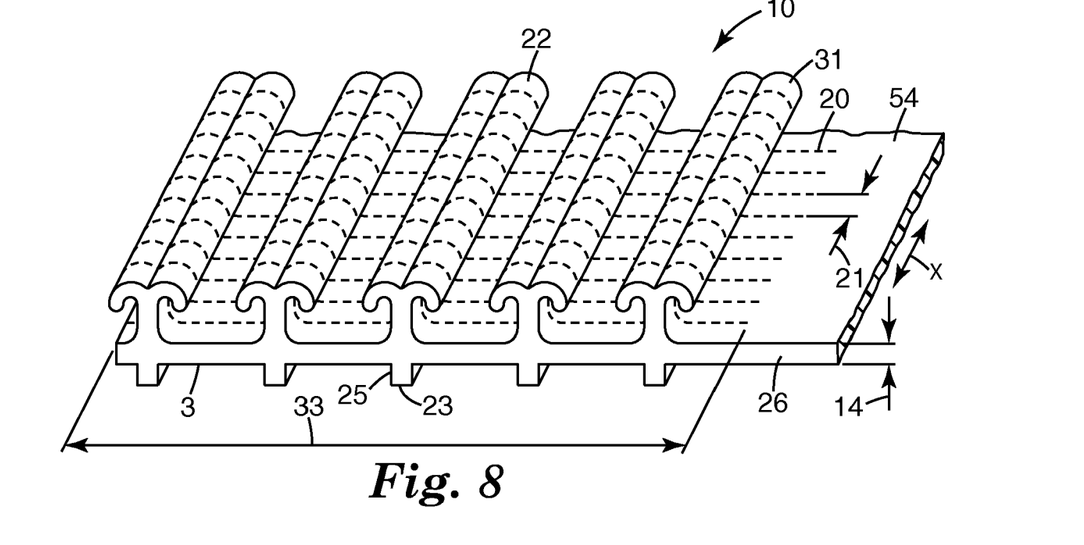
FIG. 8 is a perspective view of the FIG. 7 film cut on one face at regular intervals.

A method for forming a hook netting of the invention is schematically illustrated in FIG. 1. Generally, the method includes first extruding a profiled film section through a die plate 1, shown in FIGS. 2 and 3. The thermoplastic resin is delivered from an extruder 51 through the die 52 having die plate with a cut opening 2 having a nonplanar (i.e. three dimensional) section 33 and a substantially planar section 34 or 34'. The die opening can be cut, for example, by electron discharge machining, shaped to form film 10 with a three dimensional section 33, as shown in FIGS. 4 and 7, which would also have elongate spaced hook head shaped structures 7, 7' extending along one or both surfaces 3 and 4 of the films 10. The elongate hook head structures 7, 7' provided on one or both surfaces 3 and 4 of the film 10, can have any predetermined hook like shape, including t-shaped, j-shaped, y-shaped or like. The film 10 generally is pulled around rollers 55 through a quench tank 56 filled with a cooling liquid (e.g., water), after which the film 10 three dimensional section 33 is transversely slit or cut at spaced locations 8 along its lengths, by a cutter 58 to form discrete cut portions of the film 10 three dimensional section 33. The film 10 is not cut, or at least is not cut through the entire film, in the substantially planar backing sections 34. As shown in FIGS. 5 and 8, the distance 21 between the cut lines 20 corresponds to about the desired width 21' of the cut portions 31 to be formed, as is shown, for example, in FIGS. 6 and 9. The cuts 20 can be at any desired angle, generally from 30° to 90°, with respect to the lengthwise extension of the film (X-direction). Optionally, the film 10 can be stretched prior to cutting to provide further molecular orientation to the polymeric film 10, reducing the thickness of the film 10 and any structures on the film. The cutter can cut using any conventional means such as reciprocating or rotating blades, lasers, or water jets, however preferably the cutter uses blades oriented at an angle of about 60 to 90 degrees with respect to lengthwise extension (X direction) of the film 10.

The film 10, as shown in FIGS. 4 and 7, has a first top face 4 and a second bottom face 3 with a film thickness 14 of from 25 microns to 1000 microns, preferably 50 microns to 500 microns. The film 10 is three dimensional in section 33 where either the film base oscillates, such as by peaks (17, 45) and valleys forming substantially continuous ridges at a first upper plane 12 and a second lower plane 13 (as shown in FIGS. 1-6), and/or has discrete ridges (22,23,7) which are formed on a continuous film base or backing layer.

In the embodiment of FIGS. 1-6 by oscillating, it is meant the film itself or the continuous film backing, not just structures on the film surface, is three dimensional or nonplanar and oscillates from an upper plane 12 to a lower plane 13. The film backing oscillates around a midline 15 and the three dimensional film is characterized by a first half 6 extending on one side of the midline 15 and a second 5 half extending on the opposing side of the midline 15. The peaks (17, 45) of the ridges on the three dimensional nonplanar film backing, or the top face of the film backing, generally extends at least to the upper plane 12. The peaks of ridges or the film backing, or individual peaks can terminate below or above the upper plane 12 preferably at a point between the midline 15 and the top plane 12. The peaks 17 on the bottom face 3 of the film backing also extend generally at least to the lower plane 13. However, again the film backing plane or individual peaks can terminate above or below the lower plane 13 and preferably between the midline 15 and the lower plane 13. The peaks generally alternate from the lower plane 13 to the upper plane 12 but multiple peaks can extend, in a row, to either the upper plane or the lower plane without extending to the other half of the nonplanar film face by having the intermediate peaks only extending to the midline, or below the midline, on the same side of the midline. Generally, an oscillating nonplanar film will have at least about 2 peaks (45 and/or 17) per linear centimeter (cm) and preferably at least 5 peaks per centimeter extending up to 50 peaks per linear centimeter. Each peak preferably will extend past the midline of the film to an extent such that the underside 18 of the peak extends past the underside of 19 of the adjacent opposing peak by at least 10 microns, preferably at least 50 microns. The distance 6 or 5 between the midline and the upper plane 12 or lower plane 13 is generally about 50 microns to 1000 microns preferably about 100 microns to 500 microns.

The film of the embodiment of FIGS. 1-4 is then cut on either the upper face 4 or the lower face 3 from the upper plane 12 toward the midline 15 or from the lower plane 13 toward the midline 15, as shown, for example, in FIG. 5 in the three dimensional section 33. The cuts 20 extend from the upper or lower plane at least through the undersides 18 or 19 of the peaks 17 or 45. At least some of the peaks 17 or 45 on a face are cut and preferably all or substantially all of the peaks are cut, however without cutting through the integral planar backing section 34. The cuts 20 will preferably at least extend to the midline of a film backing. Generally the cuts can extend so that they terminate prior to the undersides (18 or 19) of the opposing peaks. Preferably, the cuts will terminate before reaching substantially all of the undersides (18 or 19) of the opposing peaks to avoid severing the film. Undersides (18 or 19) of the peaks on one face will form the valleys of the opposing face. In an alternative embodiment, the film peaks (17 or 45) can be cut on both faces as described above as long as the cuts on opposing faces are offset so as not to completely sever the film and these cuts do not cut through the planar backing section 34 as shown in FIGS. 5 and 6, leaving this section without holes or perforations The distance 21 between cuts 20, which forms the cut portions 31, is generally 100 microns to 1000 microns, preferably from 200 microns to 500 microns. The cut portions 31 form the strands 44 extending in the cross-direction of the net section 40. The strands 41 extending in the lengthwise direction are formed by the uncut portions of the nonplanar film section. These lengthwise strands 41 are generally continuous when the film backing is cut on only one face. At least some of the cross direction strands 46 are at least in part generally always continuous when the cuts are continuous. The hook elements 48 are formed by the cut hook shaped ridge 7 forming the peak 45 on the upper face 4 of the three dimensional film section 33.

After cutting of the film 10 the film is longitudinally stretched at a stretch ratio of at least 2:1 to 4:1, and preferably at a stretch ratio of at least about 3:1, preferably between a first pair of nip rollers 60 and 61 and a second pair of nip rollers 62 and 63 driven at different surface speeds preferably in the lengthwise direction. This forms the open three dimensional netting shown in, e.g., FIGS. 6 and 9. Roller 61 is typically heated to heat the film prior to stretching, and roller 62 is typically chilled to stabilize the stretched film. Optionally, the film can also be transversely stretched to provide orientation to the film in the cross direction and flatten the profile of the netting formed. The films 10 could also be stretched in other directions or in multiple directions. The above stretching method would apply to all embodiments of the invention. When the films are cut on only one face, the open areas 43, 43' generally are separated by linear strands 41, 41' which strands have a non-rectilinear cross-section or are nonplanar along their length or both. The transverse strands 44, 44' can be planar or nonplanar and they can be rectilinear in cross-section. Nonplanar strands or a nonplanar netting section provides for a more flexible netting which creates breathability both through the film (by the open area of the netting) and along the plane of the reticulated netting, due to its nonplanar nature. The open areas 43, 43' generally comprise about at least 50 percent of the surface area of the netting, excluding the non-net section, and preferably at least 60 percent. The surface area of the netting is the planar cross-sectional area of the netting in the X-Y plane. This large percentage open area creates an extremely flexible and breathable netting. The hook heads formed on hook nettings are preferably smaller than the individual openings in the netting in the direction parallel with the hook head overhangs such that the hook netting is non-self engaging.

Figure 9:
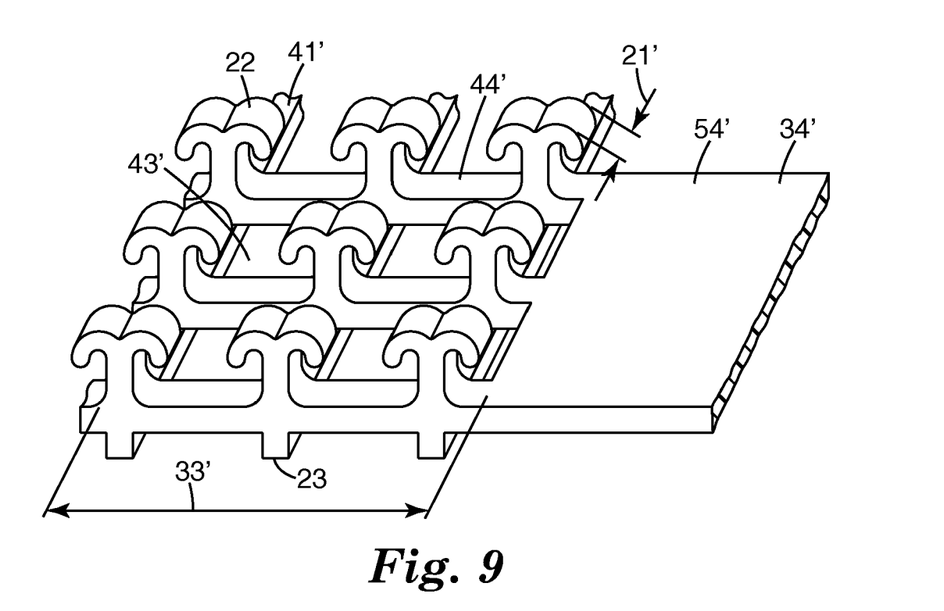
FIG. 9 is a perspective view of a netting in accordance with the present invention produced from the FIG. 8 cut film.

Stretching causes spaces 43, 43' between the cut portions 31 of the film and creates the longitudinal strands 41, 41' by orientation of the uncut portions of the film. In the embodiment of FIGS. 1-6 the transverse strands 44 are formed by interconnected cut film backing portions each of which has leg portions which join at the peak 45. In the embodiment of FIGS. 7-9 the transverse strands 44' are formed solely by the cut film backing. In the embodiment of FIGS. 1-6 the leg portions of adjacent cut portions are connected by the lengthwise strands (e.g., 41) or the uncut film portions.

FIG. 6 is an exemplary polymeric netting, which can be produced, according to the first embodiment of the present invention, generally designated by the reference numerals 40. The cut ridges 7 on the upper surface 45 form a multiplicity of hook members 48 and the uncut planar backing section forms a non-net section 34 which can be used as an attachment surface, a finger-lift or like.

The second embodiment of FIGS. 7-9 is like the first embodiment in that the film 10 is cut on the upper 4 and/or lower 3 face at least on a face provided with a hook shaped 7' ridge 22 and an opposing ridge 23. The cuts 20 extend from the top of the hook shaped 7' ridge 22 to at least the starting point 25 of the opposing ridge 23 through the film backing 26. The film backing 26 is not in the planar backing section 34, which can be accomplished by lowering section 34 or raising three-dimensional section 33 relative to the cutting blades. The cuts can extend into the opposing ridges 23 but must terminate before severing these ridges 23. A second cut could also be done on the opposing face 3 cutting into ridges 23, which may also be provided with hook shaped profiles, as long as ridges 23, and the planar backing section 34, are not cut all the way through or severed.

The netting is formed having transversely extending strands 44, 44' that are created by the cut portions of the three-dimensional section extending in the cross direction and longitudinally extending strands 41, 41' created at least in part by uncut portions of the film 10 or opposing ridges 23. When tension or stretching is applied to the film 10 in the lengthwise direction, the cut portions 31 of the film separate, as shown in the embodiments of FIGS. 6 and 9. When the film 10 is cut on only one face, the uncut portions of the film or strands, between cut lines, are aligned in the lengthwise direction resulting in formation of linear strands 41, 41' extending in the lengthwise direction upon stretching or tensioning of the cut film. The transverse strands 44, 44' are created by the cut portions 31 or the backing in the embodiments shown in FIGS. 6 and 9. The cut portions 31 connect the longitudinal strands 41, 41' formed by the uncut portions of the opposing strands 23 or the backing.

The invention netting is characterized by having no bond points or bonding material at the cross-over points of the transverse and longitudinal strands or between the net section 33' and the non-net section 34' as they are all formed of one integral film backing. The net and non-net sections (33' and 34') are integrally formed of a continuous thermoplastic material. The connection between the strand elements and the non-net section 34' is created in the film formation process where the strands are created by cutting of an integral film. As such the net at the strand cross-over points and the net non-net boundary is a continuous homogeneous polymeric phase. Namely, there are no interfacial boundaries caused by fusion or bonding of separate strand elements at the strand cross-over points or between the two sections.

Preferably, at least one set of strands and the non-net section has molecular orientation caused by stretching; this generally would be the longitudinal strands. These oriented strands could be of any cross-sectional profile and would tend to become rounded due to polymer flow during stretching. Orientation creates strength in these strands providing a dimensionally stable web in the direction of orientation with continuous linear strands. Unoriented strands are generally rectilinear in cross-section due to the cutting operation. In the embodiment of FIG. 6 the two sets of strands generally will intersect a planar face of the netting at an angle α, in the Z or thickness direction, of greater than zero (0) generally 20 degrees to 70 degrees, preferably 30 degrees to 60 degrees.

Suitable polymeric materials from which the netting of the invention can be made include thermoplastic resins comprising polyolefins, e.g. polypropylene and polyethylene, polyvinyl chloride, polystyrene, nylons, polyester such as polyethylene terephthalate and the like and copolymers and blends thereof. Preferably the resin is a polypropylene, polyethylene, polypropylene-polyethylene copolymer or blends thereof.

The netting can also be a multilayer construction such as disclosed in U.S. Pat. Nos. 5,501,675; 5,462,708; 5,354,597 and 5,344,691, the substance of which are substantially incorporated herein by reference. These references teach various forms of multilayer or coextruded elastomeric laminates, with at least one elastic layer and either one or two relatively inelastic layers. A multilayer netting could also be formed of two or more elastic layers or two or more inelastic layers, or any combination thereof, utilizing these known multilayer coextrusion techniques.

Inelastic layers are preferably formed of semicrystalline or amorphous polymers or blends. Inelastic layers can be polyolefinic, formed predominately of polymers such as polyethylene, polypropylene, polybutylene, or polyethylene-polypropylene copolymer.

Elastomeric materials which can be extruded into film include ABA block copolymers, polyurethanes, polyolefin elastomers, polyurethane elastomers, EPDM elastomers, metallocene polyolefin elastomers, polyamide elastomers, ethylene vinyl acetate elastomers, polyester elastomers, or the like. An ABA block copolymer elastomer generally is one where the A blocks are polyvinyl arene, preferably polystyrene, and the B blocks are conjugated dienes specifically lower alkylene diene. The A block is generally formed predominately of monoalkylene arenes, preferably styrenic moieties and most preferably styrene, having a block molecular weight distribution between 4,000 and 50,000. The B block(s) is generally formed predominately of conjugated dienes, and has an average molecular weight of from between about 5,000 to 500,000, which B block(s) monomers can be further hydrogenated or functionalized. The A and B blocks are conventionally configured in linear, radial or star configuration, among others, where the block copolymer contains at least one A block and one B block, but preferably contains multiple A and/or B blocks, which blocks may be the same or different. A typical block copolymer of this type is a linear ABA block copolymer where the A blocks may be the same or different, or multi-block (block copolymers having more than three blocks) copolymers having predominately A terminal blocks. These multi-block copolymers can also contain a certain proportion of AB diblock copolymer. AB diblock copolymer tends to form a more tacky elastomeric film layer. Other elastomers can be blended with a block copolymer elastomer(s) provided that they do not adversely affect the elastomeric properties of the elastic film material. A blocks can also be formed from alphamethyl styrene, t-butyl styrene and other predominately alkylated styrenes, as well as mixtures and copolymers thereof. The B block can generally be formed from isoprene, 1,3-butadiene or ethylene-butylene monomers, however, preferably is isoprene or 1,3-butadiene.

With all multilayer embodiments, layers could be used to provide specific functional properties in one or both directions of the netting or hook netting such as elasticity, softness, stiffness, bendability, roughness or the like. The layers can be directed at different locations in the Z direction and form hook element cut portions or uncut portions that are formed of different materials. For example, if a cut portion is elastic, this results in a net which is elastic in at least the transverse or cut direction. If the uncut portions are elastic this would result in a netting that may be closed but is elastic in the longitudinal direction.

The hook elements formed on the cut portions form a reticulated netting having hook engaging elements providing a breathable, compliant and deformable hook netting. A hook netting of this type is extremely desirable for limited use articles such as disposable absorbent articles (e.g., diapers, feminine hygiene articles, limited use garments and the like), particularly with the uncut nonplanar non-net section 54 forming an attachment surface. In this case the net portion would form a fastening portion of a fastening tab and have a size appropriate for this end use. The non net section would function as an attachment surface to attach to the absorbent garment and could be joined to the absorbent article such as by sonic bonding, an adhesive (which could be a pressure sensitive adhesive "PSA" coating on the non-net area). The net area could be further reinforced by attachment to a nonwoven material, which would maintain its flexibility and breathability while adding further strength and softness. A preferred method would be by hydroentangling a nonwoven with the net hook section.

EXAMPLE 1

A hook net material containing both net and non-net areas was made using apparatus similar to that shown in FIG. 1. A polypropylene/polyethylene impact copolymer (SRC7-644, 1.5 MFI, Dow Chemical) was extruded with a 6.35 cm single screw extruder (24:1 L/D) using a barrel temperature profile of 177° C.-232° C.-246° C. and a die temperature of approximately 235° C. The extrudate was extruded vertically downward through a die having an opening cut by electron discharge machining to produce an extruded profiled web (henceforth referred to as the precursor film). After being shaped by the die, the extrudate was quenched in a water tank at a speed of 6.1 meter/min with the water being maintained at approximately 10° C. The precursor film was comprised of a planar backing base layer with elongated spaced ribs projecting from both surfaces of the base layer. The precursor film was similar to that shown in FIG. 7 except that the lower ribs were the same shape as the upper ribs and they were offset between the upper ribs. Also, the film contained ribs over its entire width rather than having the flat planar backing section 34 shown in FIG. 7.

The precursor film (approximately 13 cm width) was then advanced through a cutting station possessing a vacuum shoe that ordinarily serves to keep the film flat. However, a 100 micron thick, 5 cm wide piece of silicone tape had been placed on the surface of the cutter shoe. This served to elevate the center 5 cm of the precursor film such that the cutting blades would cut deeper into the web in this area than it would in the areas that were in direct contact with the vacuum shoe. In this manner, the elevated precursor film (the three dimensional section) was passed through the cutting station such that the upper ribs and the base layer (but not the lower ribs) were transversely cut at an angle of 23 degrees measured from the transverse direction of the film, over the center 5 cm of the film which had been elevated by the silicone tape. In the surrounding areas of the film, where the film was not elevated by the silicone tape, the upper ribs only (i.e. not the base layer or lower ribs) were cut at the same 23 degree angle. The spacing of all cuts was 305 microns. After cutting the ribs, the base of the precursor film was longitudinally stretched at a stretch ratio of approximately 3.65 to 1 between a first pair of nip rolls and a second pair of nip rolls to further separate the individual hook elements to approximately 8.5 hooks/cm. There were approximately 15 rows of ribs or cut hooks per centimeter. The upper roll of the first pair of nip rolls was heated to 143 C to soften the web prior to stretching.

Where the base layer had been cut, the stretching served to generate openings so as to produce a hook net section similar to that shown in FIG. 9 (with the same differences noted as in FIG. 7). Where the base layer had not been cut, a non-net hook material (i.e. hook elements on a continuous, nonapertured backing) was produced. In this manner, a hook net was produced containing both net and non-net areas, with no bond points or bonding material between the net and non-net sections.

We claim:

1. A polymeric film hook netting comprising a continuous polymeric film backing having a net section and a second integral non-net film section, where the net section is formed of a first set of a plurality of thermoplastic strands extending in a first direction and a second set of a plurality of integral strands extending in a second direction at least one of which sets of strands has upstanding hook elements.

2. The polymeric film hook netting of claim 1 wherein the percent open area of the net section is at least 50 percent.

3. The polymeric film hook netting of claim 1 wherein the percent open area of the net section is at least 60 percent.

4. The polymeric film hook netting of claim 1 wherein the first set of strands extend in the transverse direction and are nonplanar and the second set of strands extend in the longitudinal direction and are nonrectilinear.

5. The polymeric film hook netting of claim 1 wherein at least one of said sets of strands are oriented strands.

6. The polymeric film hook netting of claim 5 wherein the other set of strands are not oriented and have a substantially rectilinear cross-section.

7. The polymeric film hook netting of claim 1 wherein at least one of said sets of strands are linear.

8. The polymeric film hook netting of claim 1 wherein both sets of strands are nonlinear.

9. The polymeric film hook netting of claim 1 wherein said hook elements extend in the direction of one of the sets of strands.

10. The polymeric film hook netting of claim 1 wherein said hook elements extend in two or more directions.

11. A fastening tab for an article comprising a polymeric film hook netting having a continuous film backing having a net section formed of plurality of a first set of thermoplastic strands extending in a first direction and a second set of integral strands extending in a second direction at least one of which strands has upstanding hook elements and a second integral non net film section for attachment to the article.

12. The fastening tab of claim 11 wherein the non net section is coated with a pressure sensitive adhesive.

13. The fastening tab of claim 11 wherein the percent open area of the net section is at least 50 percent.

14. The fastening tab of claim 11 wherein the percent open area of the netting is at least 60 percent.

15. The fastening tab of claim 11 wherein the first set of strands extend in the transverse direction and are nonplanar and the second set of strands extend in the longitudinal direction and are nonrectilinear.

16. The fastening tab of claim 11 wherein at least one of said sets of strands are oriented strands.

17. The fastening tab of claim 16 wherein the other set of strands are not oriented and have a substantially rectilinear cross-section.

18. The polymeric film hook netting of claim 17 wherein said hook elements extend in the direction of one of the sets of strands.

* * * * *

UNITED STATES PATENT AND TRADEMARK OFFICE
CERTIFICATE OF CORRECTION

PATENT NO.        : 7,622,180 B2                                    Page 1 of 1
APPLICATION NO.   : 11/456234
DATED             : November 24, 2009
INVENTOR(S)       : Seth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 388 days.

Signed and Sealed this

Twenty-sixth Day of October, 2010

David J. Kappos
*Director of the United States Patent and Trademark Office*